US008300090B2

(12) United States Patent
Mitsuhashi

(10) Patent No.: US 8,300,090 B2
(45) Date of Patent: Oct. 30, 2012

(54) IN-VIVO IMAGE ACQUIRING SYSTEM, IN-VIVO IMAGE PROCESSING METHOD, AND BODY-INSERTABLE APPARATUS

(75) Inventor: Kei Mitsuhashi, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 778 days.

(21) Appl. No.: 12/199,679

(22) Filed: Aug. 27, 2008

(65) Prior Publication Data

US 2009/0058996 A1  Mar. 5, 2009

(30) Foreign Application Priority Data

Aug. 31, 2007  (JP) .................................. 2007-226973

(51) Int. Cl.
 *H04N 7/18* (2006.01)
(52) U.S. Cl. ........................................................ 348/65
(58) Field of Classification Search .................. 348/65
 See application file for complete search history.

(56) References Cited

U.S. PATENT DOCUMENTS

| 7,567,692 | B2* | 7/2009 | Buzaglo et al. | 382/128 |
|---|---|---|---|---|
| 7,697,970 | B2* | 4/2010 | Uchiyama et al. | 600/407 |
| 7,704,204 | B2* | 4/2010 | Shigemori et al. | 600/109 |
| 2002/0118278 | A1* | 8/2002 | Kobayashi et al. | 348/65 |
| 2003/0020810 | A1* | 1/2003 | Takizawa et al. | 348/68 |
| 2005/0029437 | A1* | 2/2005 | Hasegawa et al. | 250/226 |
| 2005/0085697 | A1* | 4/2005 | Yokoi et al. | 600/160 |
| 2006/0050145 | A1* | 3/2006 | Tanimoto | 348/68 |
| 2006/0083438 | A1* | 4/2006 | Donomae et al. | 382/254 |
| 2006/0209185 | A1* | 9/2006 | Yokoi | 348/65 |
| 2006/0238614 | A1* | 10/2006 | Konno | 348/69 |
| 2007/0066868 | A1* | 3/2007 | Shikii | 600/118 |
| 2007/0078300 | A1* | 4/2007 | Zinaty et al. | 600/102 |
| 2007/0252893 | A1* | 11/2007 | Shigemori | 348/65 |
| 2007/0282169 | A1* | 12/2007 | Tsujita | 600/160 |
| 2008/0262313 | A1* | 10/2008 | Shimizu et al. | 600/160 |
| 2010/0007724 | A1* | 1/2010 | Takayama | 348/65 |
| 2010/0016661 | A1* | 1/2010 | Nagase et al. | 600/109 |
| 2010/0045786 | A1* | 2/2010 | Kitamura | 348/65 |
| 2010/0208047 | A1* | 8/2010 | Kitamura | 348/65 |
| 2012/0002026 | A1* | 1/2012 | Honda et al. | 348/65 |

FOREIGN PATENT DOCUMENTS

| JP | 2003-019111 | 1/2003 |
|---|---|---|
| JP | 2006-115965 | 5/2006 |
| JP | 2006-304885 A | 11/2006 |
| JP | 2007-235723 | 9/2007 |

* cited by examiner

*Primary Examiner* — Imad Hussain
(74) *Attorney, Agent, or Firm* — Scully, Scott, Murphy & Presser, P.C.

(57) ABSTRACT

An in-vivo image acquiring system having a body-insertable apparatus and a processing apparatus. The body-insertable apparatus has an imaging unit which captures images of the inside of the subject, and a transmitting unit which attaches type information to the image information and transmits the image information to the outside of the subject. The processing apparatus has an image processing unit which acquires optical information corresponding to the type information attached to image information to be processed and processes the image information to be processed using an image processing program which corresponds to the acquired optical information. The type information indicates an applied portion of the body-insertable apparatus. The processing apparatus also processes image information corresponding to portions other than the applied portions of the body-insertable apparatus as image information to be processed.

4 Claims, 10 Drawing Sheets

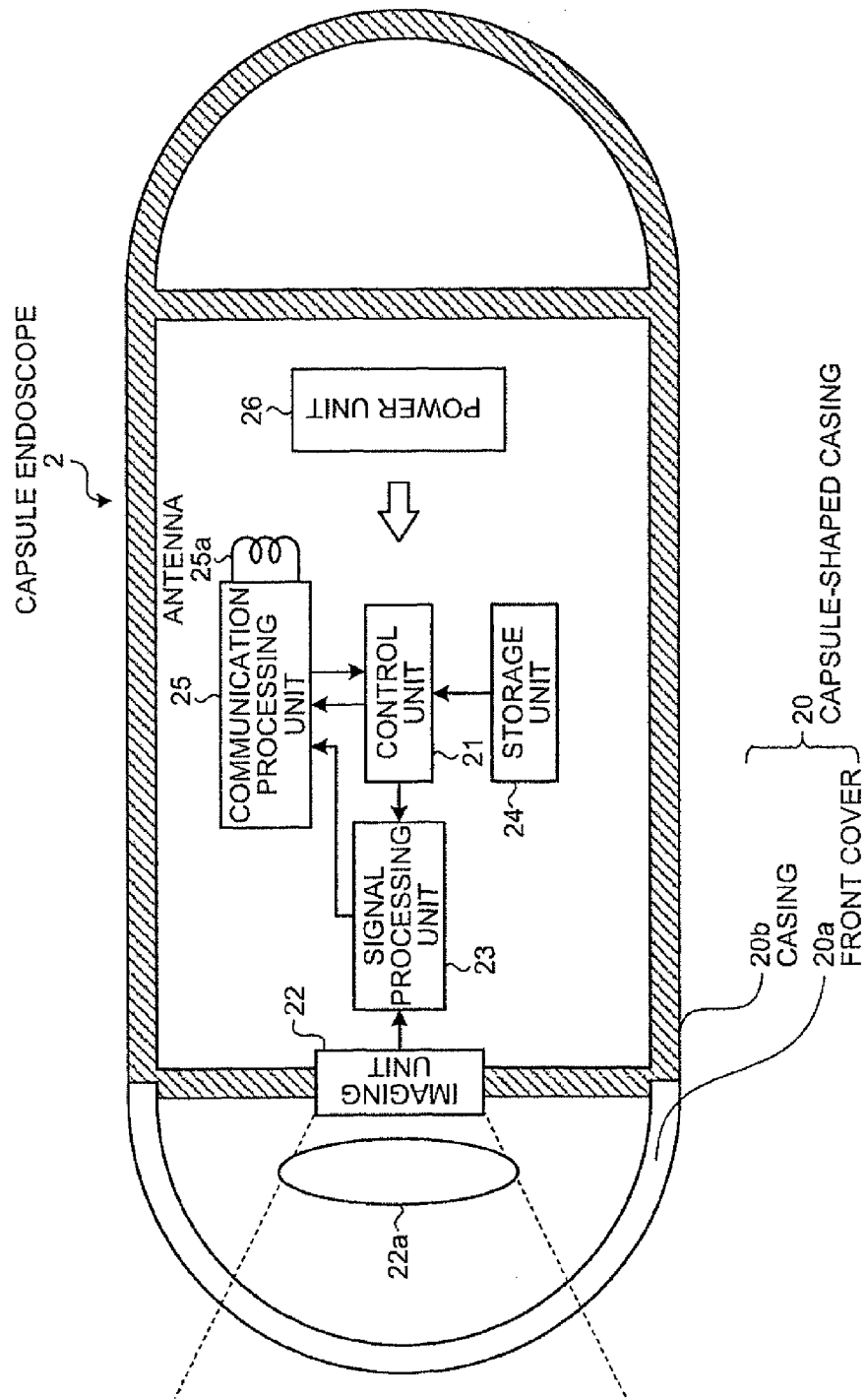

FIG.3

| | PREAMBLE | VD | DUMMY | IMAGE | |
|---|---|---|---|---|---|
| G1 | H BLANK | HD | DUMMY | IMAGE | |
| | H BLANK | HD | DUMMY | IMAGE | |
| | H BLANK | HD | DUMMY | IMAGE | |
| | H BLANK | HD | DUMMY | IMAGE | |
| | H BLANK | HD | DUMMY | IMAGE | |
| | H BLANK | HD | DUMMY | IMAGE | |
| | H BLANK | HD | DUMMY | IMAGE | |
| | H BLANK | HD | DUMMY | IMAGE | |
| | H BLANK | HD | DUMMY | IMAGE | Da |
| | H BLANK | HD | DUMMY | IMAGE | |
| | PREAMBLE | VD | DUMMY | IMAGE | UNIQUE INFORMATION |
| G2 | H BLANK | HD | DUMMY | IMAGE | |
| | H BLANK | HD | DUMMY | IMAGE | |
| | H BLANK | HD | DUMMY | IMAGE | |
| | H BLANK | HD | DUMMY | IMAGE | |
| | H BLANK | HD | DUMMY | IMAGE | |
| | H BLANK | HD | DUMMY | IMAGE | |
| | H BLANK | HD | DUMMY | IMAGE | |
| | H BLANK | HD | DUMMY | IMAGE | Da |
| | H BLANK | HD | DUMMY | IMAGE | |
| | H BLANK | HD | DUMMY | IMAGE | UNIQUE INFORMATION |

⋮

| | PREAMBLE | VD | DUMMY | IMAGE | |
|---|---|---|---|---|---|
| Gn | H BLANK | HD | DUMMY | IMAGE | |
| | H BLANK | HD | DUMMY | IMAGE | |
| | H BLANK | HD | DUMMY | IMAGE | |
| | H BLANK | HD | DUMMY | IMAGE | |
| | H BLANK | HD | DUMMY | IMAGE | |
| | H BLANK | HD | DUMMY | IMAGE | |
| | H BLANK | HD | DUMMY | IMAGE | |
| | H BLANK | HD | DUMMY | IMAGE | |
| | H BLANK | HD | DUMMY | IMAGE | Da |
| | H BLANK | HD | DUMMY | IMAGE | UNIQUE INFORMATION |

FIG.5

| TYPE | VERSION | OPTICAL INFORMATION ||||||| 
|---|---|---|---|---|---|---|---|---|
| | | MAGNIFI-CATION RATIO | DT VALUE | PIXEL VALUE | LUMI-NANCE | ABERRATION TO HEIGHT OF IMAGE | γ | SPECTRAL SENSITIVITY |
| SMALL INTESTINE | 1.0 | A1 | B1 | C1 | D1 | E1 | F1 | G2 |
| | 1.1 | A2 | B2 | C2 | D2 | E2 | F2 | G2 |
| | 1.2 | A3 | B3 | C3 | D3 | E3 | F3 | G2 |
| | 2.0 | A4 | B4 | C4 | D4 | E4 | F4 | G2 |
| STOMACH | 3.0 | A5 | B5 | C5 | D5 | E5 | F5 | G2 |
| | 3.1 | A6 | B6 | C6 | D6 | E6 | F6 | G2 |
| | 3.2 | A7 | B7 | C7 | D7 | E7 | F7 | G2 |
| | 4.0 | A8 | B8 | C8 | D8 | E8 | F8 | G2 |

FIG.6

| IMAGE PROCESSING PROGRAM ||||||| 
|---|---|---|---|---|---|---|
| MAGNIFICA-TION-RATIO-ADJUSTING PROGRAM | DT-VALUE-CORRECTING PROGRAM | SHARPENING PROGRAM | LUMINANCE-ADJUSTING PROGRAM | ABERRATION-CORRECTING PROGRAM | γ-CORRECTING PROGRAM | COLOR-CORRECTING PROGRAM |
| a1 | b1 | c1 | d1 | e1 | f1 | g1 |
| a2 | b2 | c2 | d2 | e2 | f2 | g2 |

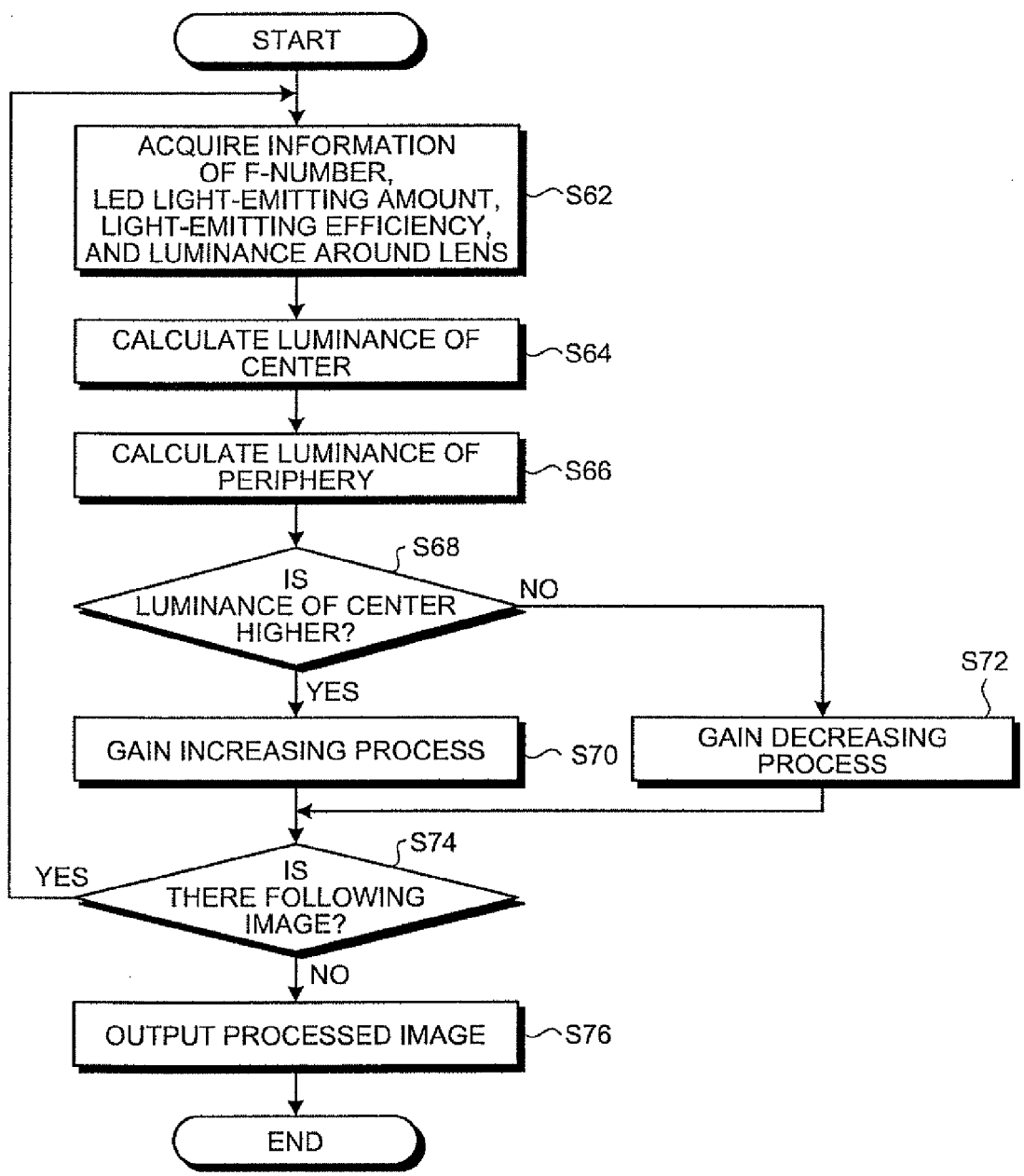

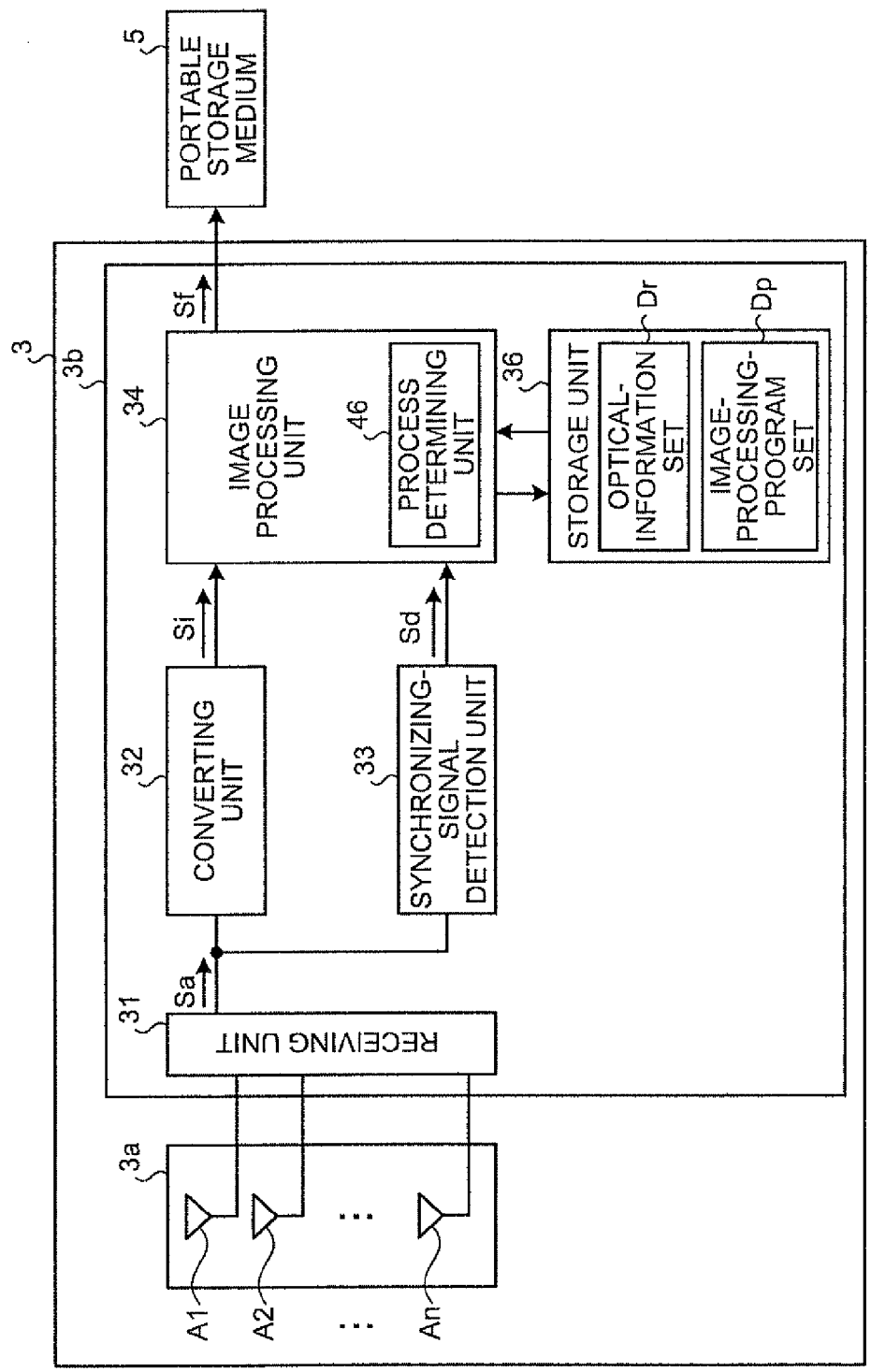

IN-VIVO IMAGE ACQUIRING SYSTEM, IN-VIVO IMAGE PROCESSING METHOD, AND BODY-INSERTABLE APPARATUS

CROSS-REFERENCE TO RELATED APPLICATIONS

This application is based upon and claims the benefit of priority from Japanese Patent Application No. 2007-226973, filed Aug. 31, 2007, the entire contents of which are incorporated herein by reference.

BACKGROUND OF THE INVENTION

1. Field of the Invention

The present invention relates to an in-vivo image acquiring system which acquires an image of an inside of a subject, an in-vivo image processing method, and a body-insertable apparatus.

2. Description of the Related Art

Recently, a swallowable capsule endoscope has been developed in a field of endoscope. The capsule endoscope has an imaging function and a wireless-transmission function, and has a mechanism such that the capsule endoscope is swallowed from a mouth of a patient for observing an inside of a body cavity, and successively captures an inside of organs such as an esophagus, a stomach, and a small intestine due to a peristalsis until naturally excreted (e.g., see Japanese Patent Application Laid-Open No. 2003-19111).

Image data captured by the capsule endoscope inside a body is successively transmitted to an outside of the body via a wireless transmission while the capsule endoscope moves through the body cavity, and then stored in a memory in a receiving apparatus arranged outside the body. A doctor or a nurse can have a diagnosis with the image data stored in the memory being displayed on a display.

The capsule endoscope described has a lens and a signal processing function which are designed with optical performance corresponding to the applied area. For example, in the capsule endoscope for a small intestine, the lens and the signal processing function are designed with the optical performance where a focus meets at a near point for observing a wall surface of the small intestine having a small inner diameter. Further, the capsule endoscope generally captures organs other than the applied area of the capsule endoscope, and transmits a huge number of images until naturally excreted.

In the conventional capsule endoscope, however, the optical performance is designed corresponding to the applied area, and the appropriate optical performance is not guaranteed for organs other than the applied area. Images of the organs other than the applied area are captured not properly enough to be able to be examined, and the images cannot be used for the examination. Thus, all images but those of the applied area in the huge number of images captured by the capsule endoscope are wasted. Further, when the images of organs other than the applied area need to be taken, the subject has to swallow the capsule endoscope which is designed with the optical performance to be able to capture the organs to be captured again, and the burden of the subject is increased.

SUMMARY OF THE INVENTION

An object of the present invention is to solve at least above-mentioned problems.

An in-vivo image acquiring system according to the present invention includes a body-insertable apparatus which is introduced inside a subject, and wirelessly transmits image information including captured images of an inside of the subject to an outside, and a processing apparatus which processes the image information wirelessly transmitted from the body-insertable apparatus, and the body-insertable apparatus including an imaging unit which captures images of the inside of the subject, and a transmitting unit which attaches type information which corresponds to optical information in the imaging unit to the image information including the images captured by the imaging unit, and transmits the image information, and the processing apparatus including a storage unit which stores combinations of each piece of the optical information corresponding to each piece of type information, and image processing programs corresponding to each piece of the optical information, and an image processing unit which acquires the optical information corresponding to the type information which is attached to the image information to be processed from the optical information stored in the storage unit, and processes the image information to be processed using the image processing program, of the image processing programs stored in the storage unit, that corresponds to the acquired optical information.

Further, an in-vivo image processing method according to the present invention is for processing image information including the images of the inside of the subject which are wirelessly transmitted from the body-insertable apparatus introduced inside the subject. The method includes the steps of capturing the images of the inside of the subject by the imaging unit in the body-insertable apparatus, transmitting the image information to which the type information corresponding to the optical information in the imaging unit is attached from the body-insertable apparatus, receiving the image information transmitted from the body-insertable apparatus, and acquiring the optical information corresponding to the type information attached to the image information to be processed from the received image information, and processing image information to be processed using the image processing program corresponding to the acquired optical information.

Further, a body-insertable apparatus which is introduced inside a subject, and wirelessly transmits image information including captured images of an inside of the subject to an outside includes an imaging unit which captures images of the inside of the subject, and a transmitting unit which attaches type information which corresponds to optical information in the imaging unit to the image information including the images captured by the imaging unit, and transmits the image information.

The above and other objects, features, and advantages of this invention will be better understood by reading the following detailed description of presently preferred embodiments of the invention, when considered in connection with the accompanying drawings.

BRIEF DESCRIPTION OF THE DRAWINGS

FIG. 2 is a block diagram of a configuration of a capsule endoscope shown in FIG. 1;

FIG. 3 is an explanatory diagram of an image signal transmitted from the capsule endoscope shown in FIG. 1;

FIG. 5 is a diagram illustrating a optical-information-set stored in a storage unit shown in FIG. 4;

FIG. 6 is a diagram illustrating a image-processing-program set stored in the storage unit shown in FIG. 4;

FIG. 10 is a flowchart showing an example of the image processing procedure performed by the image processing unit shown in FIG. 4; and FIG. 11 is a block diagram of a configuration of a receiving apparatus shown in FIG. 1.

DETAILED DESCRIPTION OF THE PREFERRED EMBODIMENTS

Exemplary embodiments of a wireless-transmission in-vivo image acquiring system and a body-inserting apparatus of the present invention (referred to below simply as "embodiments") are described with reference to the drawings. The present invention is not limited to the embodiments. Further, same numerals are attached to identical components.
[Configuration of In-Vivo Image Acquiring System]

Figure 1:
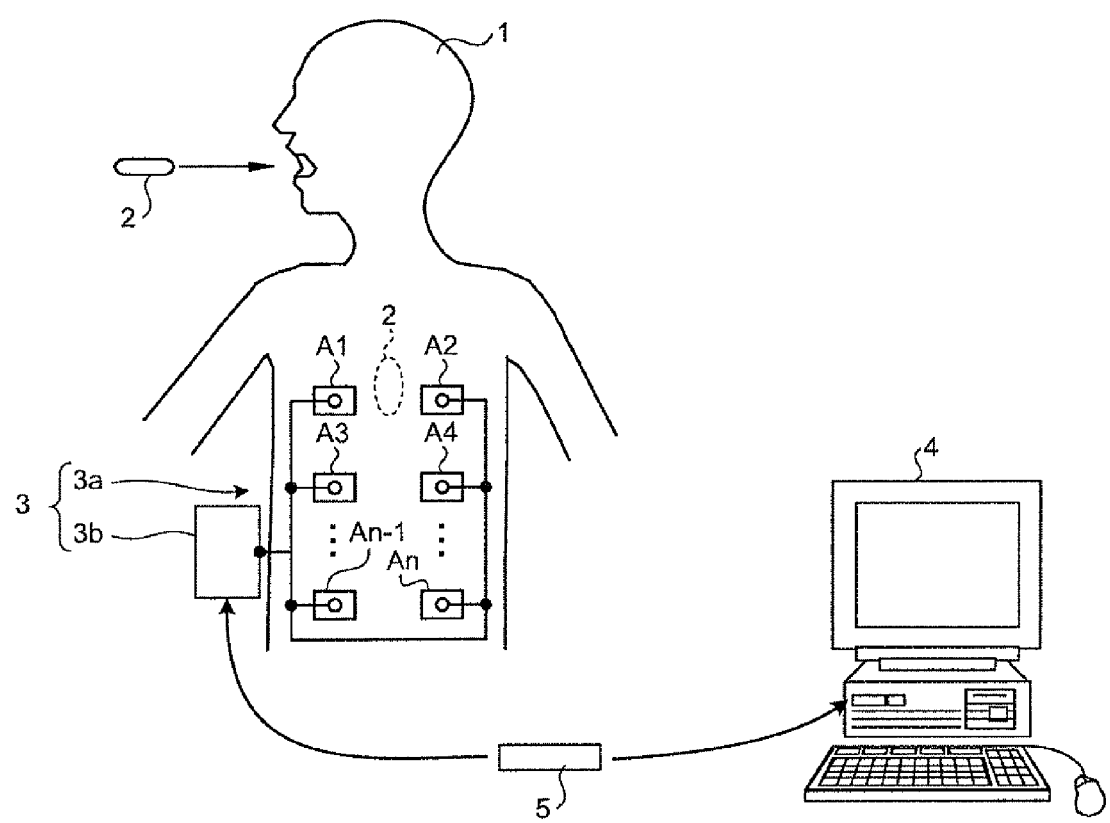
FIG. 1 is a schematic diagram of an overall configuration of an in-vivo image acquiring system according to an embodiment.

The embodiment of the present invention is described. FIG. 1 is a schematic diagram of an overall configuration of an in-vivo image acquiring system according to an embodiment. The in-vivo image acquiring system employs a monocular capsule endoscope as an example of a body-inserting apparatus. As shown in FIG. 1, the wireless in-vivo image acquiring system includes a capsule endoscope 2 which is introduced inside a subject 1 and captures intracelomic images, and wirelessly transmits data such as an image signal to a receiving apparatus 3, a receiving apparatus which receives the data of the intracelomic images wirelessly transmitted from the capsule endoscope 2, a processing apparatus 4 which displays the intracelomic images based on the image signal received by the receiving apparatus 3, and a portable storage medium 5 used for transferring data between the receiving apparatus 3 and the processing apparatus 4.

Further, the receiving apparatus 3 includes a wireless-transmission unit 3a which includes plural receiving antennas A1 to An attached to an outer surface of the subject 1, and a main receiving unit 3b which processes a wireless-transmission signal received via the plural receiving antennas A1 to An and performs other processes. Those units are detachably connected with the receiving apparatus 3 via a connector or the like. Alternatively, the receiving antennas A1 to An may be attached to, for example, a jacket which can be worn by the subject 1 and the subject 1 may wear the jacket so that the receiving antennas are attached to the subject 1. Further, in this case, the receiving antennas A1 to An may be detachably attached to the jacket.

The processing apparatus 4 displays the intracelomic images captured by the capsule endoscope 2. The processing apparatus 4 may be realized by a workstation or the like which displays the images based on the data acquired via the portable storage medium 5. Specifically, the processing apparatus 4 may be realized by a CRT display or an LCD display or the like which displays the image thereon, or a printer or the like which outputs the image on other mediums.

The portable storage medium 5 may be realized by a compact flash (registered trademark) or the like, and detachably attached to the main receiving unit 3b and the processing apparatus 4. The portable storage medium 5 can output or store information when attached to the main receiving unit 3b and the processing apparatus 4. Specifically, the portable storage medium 5 may be attached to the main receiving unit 3b and while the capsule endoscope 2 moves through the body cavity of the subject 1, and the portable storage medium 5 stores therein the data transmitted from the capsule endoscope 2. Further, after the capsule endoscope 2 is excreted from the subject 1, that is, after the capturing of the inside of the subject 1 is finished, the portable storage medium 5 is detached from the main receiving unit 3b and attached to the processing apparatus 4 so that the data may be read out by the processing apparatus 4. Since the data is transferred via the portable storage medium 5 between the main receiving unit 3b and the processing apparatus 4, the subject 1 can act freely while the inside of the body cavity is captured, and the time for transferring the data to the processing apparatus 4 can be shortened. Further, data transfer between the main receiving unit 3b and the processing apparatus 4 may be performed by other storage apparatuses built into the main receiving unit 3b and the main receiving unit 3b may have a wired or wireless connection with the processing apparatus 4.
[Configuration of Body-Insertable Apparatus]

A configuration of the capsule endoscope 2 which is an example of the body-insertable apparatus according to the present invention is described. FIG. 2 is a schematic diagram showing an example of the configuration of the capsule endoscope 2. As shown in FIG. 2, the capsule endoscope 2 includes an imaging unit 22 which captures the body cavity of the subject 1, and the power unit 26 which supplies power for each component forming the capsule endoscope 2 inside a capsule-shaped casing 20. Further, although the imaging unit 22 shown in FIG. 2 is monocular, the imaging unit 22 may be binocular with plural imaging units 22.

The capsule-shaped casing 20 includes a transparent dome-shaped front cover 20a, and a casing 20b which is kept watertight with the front cover 20a. The capsule-shaped casing 20 is of a size to be swallowed by the mouth of the subject 1. The front cover 20a is attached to one end of the casing 20b. The casing 20b is made of a colored material which does not transmit light. The casing 20b contains a control unit 21 which controls driving of each component of the capsule endoscope 2 and controls input and output of signals of each component, an imaging unit 22 which captures an inside of the body cavity, a signal processing unit 23 which processes the image captured by the imaging unit 22, a storage unit 24 which stores the information needed for the wireless transmission, a communication processing unit 25 which modulates each signal to be transmitted to the processing apparatus 4 arranged outside into a wireless-transmission signal and demodulates the wireless-transmission signal received via an antenna 25a, and a power unit 26 which supplies driving power for each component of the capsule endoscope 2. The communication processing unit 25 includes the antenna 25a which may be realized by a coiled antenna, and transmits and receives the wireless-transmission signal to and from the antenna arranged outside.

The imaging unit 22 captures the image of the body cavity of the subject 1. Specifically, the imaging unit 22 is realized by an imaging device such as a CCD and CMOS, a light-emitting device such as an LED which illuminates an imaged field of the imaging device, and a optical components such as a lens 22a which forms an image of the reflected light which is transmitted from the imaged field to the imaging device. The imaging unit 22 is fixated on an edge of the casing 20b. The imaging unit 22 forms the image of the reflected light which is received from the imaged field via the front cover 20a, and captures the image inside the body cavity of the subject 1. The imaging device, the light-emitting device, and the optical components such as the lens 22a in the imaging unit 22 have a function and a lens which are designed with optical performance corresponding to an applied area of the capsule endoscope 2. For example, when the capsule endoscope is to be used for a small intestine, the lens and the signal processing function and the like in the imaging unit 22 are designed with the optical performance to focus on a point nearby so that the wall surface of the small intestine, which has a small inner diameter, can be captured. Further, when the capsule endoscope 2 is to be used for a stomach, the lens and the signal processing function are designed with optical performance to focus on a point far from the capsule endoscope 2 compared with the case of the small intestine so that the inside of the stomach, which has a large volume, can be captured.

The capsule endoscope 2 attached type information corresponding to the optical information to image information including in-vivo images, and transmits the image information. The imaging unit 22 of the capsule endoscope 2 is designed with optical performance corresponding to the applied area of the capsule endoscope 2, and thus each pieces of optical information of the imaging unit 22 differs corresponding to the applied area. The capsule endoscope 2 attaches information of the applied area of the capsule endoscope 2 to the image information as the type information corresponding to the optical information of the imaging unit 22 in the capsule endoscope 2, and transmits the image information.

The type information is previously stored in the storage unit 24. The control unit 21 acquires the type information corresponding to the applied area of the imaging unit 22 from the storage unit 24, and outputs the type information to the signal processing unit 23. The signal processing unit 23 processes the image captured by the imaging unit 22, and attaches the type information which is output from the control unit 21 to the image signal including the image.

Specifically, as shown in FIG. 3, the signal processing unit 23 processes an image G1 captured by the imaging unit 22 for every unit of scan-line data. Further, the signal processing unit 23 appends unique information Da including information which is identical for the capsule endoscope 2 to an end of last scan-line data. The unique information Da includes white-balance information, a serial number of the capsule endoscope 2, and the like, and further includes the above-described type information. The signal processing unit 23 appends the unique information Da including the white-balance information, the serial number, and the type information to an end of the last scan-line data similarly for images G2 to Gn captured by the imaging unit 22.

The communication processing unit 25 wirelessly transmits the information generated by the signal processing unit 23 via the antenna 25a. Specifically, the communication processing unit 25 attaches the type information corresponding to the optical information in the imaging unit 22 to the image information including images captured by the imaging unit 22, and wirelessly transmits the image information to an outside.

Thus, the capsule endoscope 2 attaches the type information, which corresponds to the optical information in the imaging unit 22 of the capsule endoscope 2 and indicates the applied area of the capsule endoscope 2, to the image information captured by the imaging unit 22. The information transmitted from the capsule endoscope 2 is received by the receiving apparatus 3, and stored in the portable storage medium 5. The processing apparatus 4 can acquire the type information with the image information including the images captured by the capsule endoscope 2 by reading the information stored in the portable storage medium 5.

[Configuration of Processing Apparatus]

Figure 4:
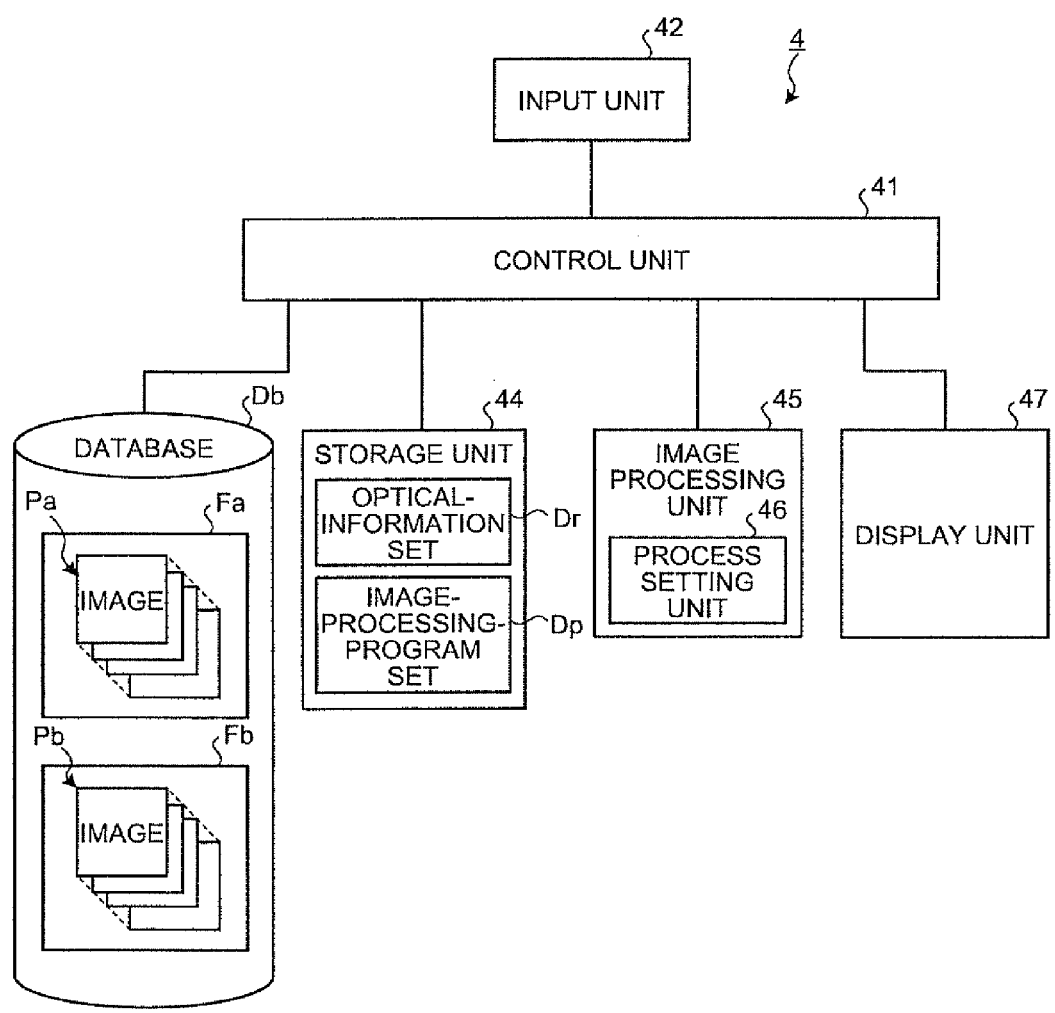
FIG. 4 is a block diagram of a configuration of a processing apparatus shown in FIG. 1.

The processing apparatus 4 shown in FIG. 1 is described with reference to FIG. 4. FIG. 4 is a block diagram of an overall configuration of the processing apparatus 4 shown in FIG. 1. As shown in FIG. 4, the processing apparatus 4 includes a control unit 41, an input unit 42, a storage unit 44, an image processing unit 45, and a display unit 47. Further, the control unit 41 has a connection with database Db where image groups Pa, Pb captured by the capsule endoscope 2 are stored in folders Fa, Fb, or the like.

The control unit 41 includes a CPU or the like which has a controlling function. The control unit 41 controls operations and procedures of the input unit 42, the storage unit 44, the image processing unit 45, and the display unit 47. The input unit 42 is realized by a keyboard to input various information, or a mouse to point to any location on a display screen of the display unit 47. The input unit 42 acquires various information needed for an analysis of the specimen, and instruction information of an analyzing operation, or the like from an outside.

The storage unit 44 includes a hard disk, which magnetically stores information, and a memory, which loads a variety of programs for a process of the processing apparatus 4 from the hard disk and electrically stores the programs therein when the processing apparatus 4 performs the process. The storage unit 44 stores various information including an optical-information set Dr and an image-processing-program set Dp. The storage unit 44 may include an auxiliary storage apparatus which can read information stored in a storage medium such as a CD-ROM, a DVD-ROM, and a PC card.

The imaging unit 22 of the capsule endoscope 2 is designed corresponding to the applied area of the capsule endoscope 2. Thus, each optical information of the imaging unit 22 differs depending on the applied area of the capsule endoscope 2, i.e., the type of capsule endoscope 2. As shown in FIG. 5, the storage unit 44 stores a table T1 which shows combinations of optical information corresponding to each type of the capsule endoscope 2 as an optical-information set Dr. The table T1 shows a magnification ratio of the imaging, a distortion (DT) value, the number of pixels, a luminance, an aberration amount for a height of an image, a gamma value, and a spectral sensitivity in the imaging unit corresponding to each type of the capsule endoscope 2, i.e., each applied area of the capsule endoscope 2 such as a small intestine as optical information. Further, when optical information differs for each version of each type of the capsule endoscope 2, the storage unit 44 stores each optical information corresponding to each version of each type as the optical-information set Dr similarly to the table T1.

The storage unit 44 stores a magnification-ratio-adjusting program which adjusts a magnification ratio of an image to be processed, a sharpening program which adjusts sharpness of the image to be processed, and a luminance-adjusting program which adjusts luminance of the image to be processed, and the like as an image-processing-program set Dp. Specifically, as shown in a table T2 in FIG. 6, the storage unit 44 stores the magnification-ratio-adjusting program which adjusts the magnification ratio of the image based on the magnification ratio of imaging of the imaging unit 22 which has captured the image to be processed, the sharpening program which adjusts sharpness of the image based on the number of pixels of the imaging unit 22 which has captured the image to be processed, and the luminance-adjusting program which adjusts luminance of the image based on the luminance of the imaging unit 22 which has captured the image to be processed as the image processing programs. Further, the storage unit 44 stores a DT-value-correcting program which corrects the image based on a DT value of the imaging unit 22 which has captured the image to be processed, an aberration-correcting program which corrects the image based on an aberration amount of the imaging unit 22 which has captured the image to be processed, a gamma-correcting program which corrects the image based on a gamma value of the imaging unit 22, and a color-correcting program which corrects colors of the image based on spectral sensitivity of the imaging unit 22 which has captured the image to be processed. The storage unit 44 may store plural image processing programs as the image-processing-program set Dp, respectively. As shown in the table T2 in FIG. 6, the storage unit 44 may store the magnification-ratio-adjusting programs a1, a2, the DT-value-correcting programs b1, b2, the sharpening programs c1, c2, the luminance-adjusting programs d1, d2, the aberration-correcting programs e1, e2, the gamma-correcting programs f1, f2, and the color-correcting programs g1, g2.

The image processing unit 45 includes a process setting unit 46. The process setting unit 46 acquires the optical information corresponding to the type information attached to the image information to be processed from the optical information stored in the storage unit 44. Further, the process setting unit 46 sets the image processing program, of the image processing programs stored in the storage unit 44, that corresponds to the optical information acquired from the image processing program stored in the storage unit 44 as the image processing program to process the image information to be processed. The image processing unit 45 processes the image to be processed using the image processing program which is set by the process setting unit and corresponds to the optical information of the image information to be processed. The image processing unit 45 processes the image information including the images corresponding to portions other than the applied area of the capsule endoscope 2 as the image information to be processed. The image processing unit 45 processes the image information to be processed using the magnification-ratio-adjusting program, the sharpening program, the luminance-adjusting program, and the like corresponding to the optical information such as the magnification ratio, the number of pixels, and the luminance corresponding to the type information of the image information to be processed. The image processing unit 45 acquires the optical information corresponding to the type information of the images which are captured by the capsule endoscope 2 and correspond to portions other than the applied area of the capsule endoscope 2, and further the image processing unit 45 processes the image using the image processing program corresponding to the optical information so that the images which correspond to portions other than the applied area and could not be used otherwise as they were can be used.

The display unit 47 is realized by a CRT display, an LCD display, and the like. The display unit 47 displays the instruction information, an instruction result, and the like of the input unit 42. The display unit 47 displays the images captured by the capsule endoscope 2 and the images processed by the image processing unit 45 under the control by the control unit 41.

[Image Processing Procedure in Processing Apparatus]

Figure 7:
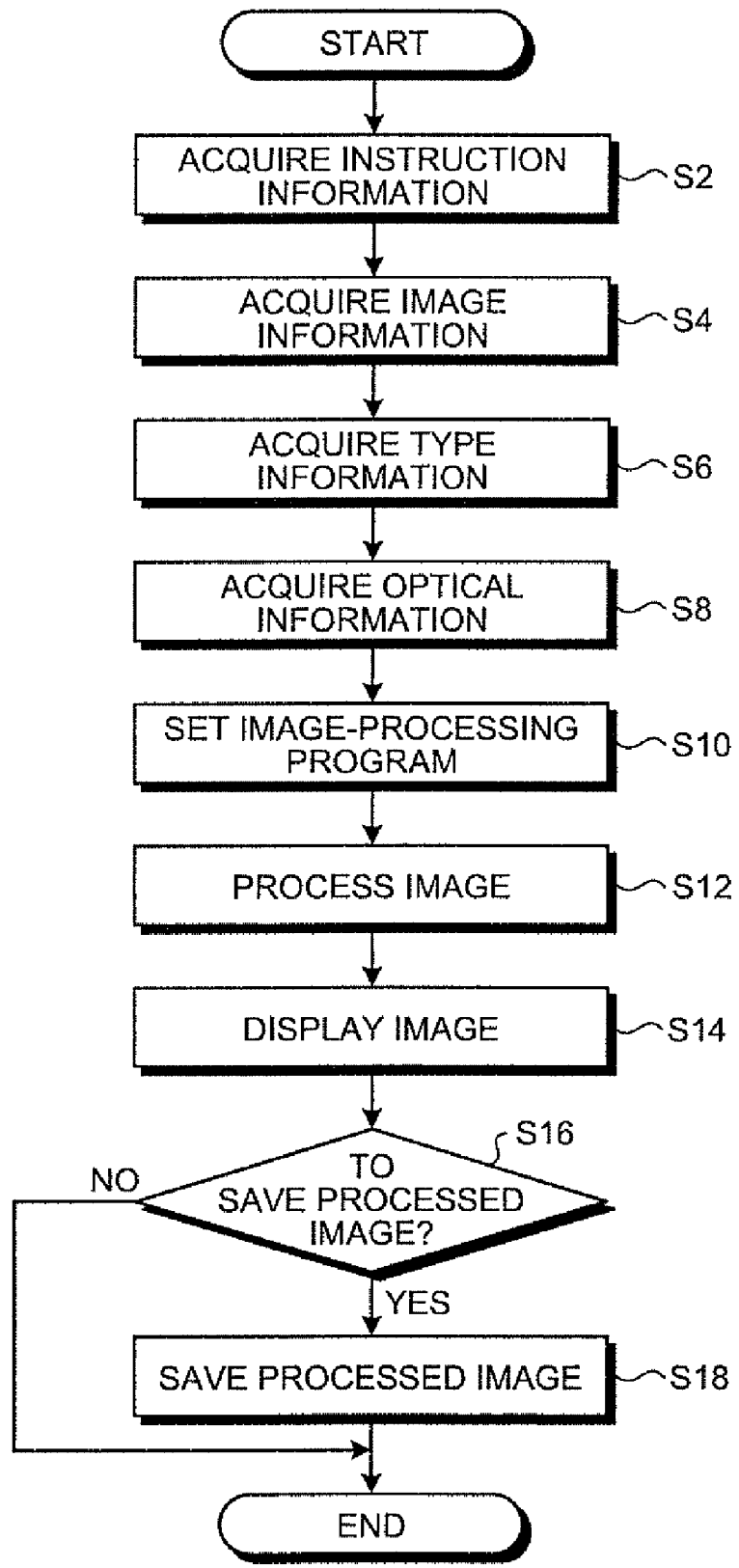
FIG. 7 is a flowchart showing a procedure of an image processing of a processing apparatus shown in FIG. 4.

The procedure of image processing in the processing apparatus 4 is described with reference to FIG. 7. FIG. 7 is a flowchart showing each procedure of the image processing in the processing apparatus 4 shown in FIG. 4. As shown in FIG. 7, the image processing unit 45 acquires via the control unit 41 instruction information which is input from the input unit 42 and which instructs the image processing unit 45 to process the image (Step S2). The instruction information includes information of the image information to be processed and the contents of the process on the image information to be processed, and the like. The instruction information instructs the image processing unit 45 to process the image information, of the image groups acquired via the portable storage medium 5, which corresponds to a predetermined number of the images corresponding to portions other than the applied area of the capsule endoscope 2. Furthermore, the instruction information instructs the image processing unit 45 to process the image information, of image groups Pa, Pb stored in database Db, that corresponds to the predetermined number of images corresponding to portions other than the applied area of the capsule endoscope 2 which has captured the image group Pa, Pb. Then, the instruction information instructs the image processing unit 45 to perform the image processing which allows the portion captured in the image which is selected as the image information to be processed according to the instruction information to be used for a diagnosis. For example, the instruction information selects the images inside the stomach observed by the capsule endoscope 2 for observing the small intestine as the image information to be processed, and instructs the image processing unit 45 to process the images so as to allow the images to be observed as easily as the images captured by the capsule endoscope 2 for observing the stomach.

The image processing unit 45 acquires the image information to be processed according to the instruction information (Step S4). The process setting unit 46 acquires the type information attached to the image information from the image information to be processed (Step S6). The type information is included in the unique information Da which is appended to the end of the last scan-line data as previously described. The process setting unit 46 acquires the optical information that corresponds to the type information of the image information to be processed that is acquired from the unique information Da appended to the end of the last scan-line data at Step 6 (Step 8).

The process setting unit 46 sets the image processing program, of the image processing programs set by the process setting unit 46, that corresponds to the acquired optical information as the image processing program to process the image information to be processed (Step S10).

The image processing unit 45 processes the image information to be processed using the image processing program set by the process setting unit 46 (Step S12). The display unit outputs and displays the image processed by the image processing unit 45 (Step S14). The control unit 41 determines whether the image processed by the image processing unit 45 is to be saved based on the instruction information which is input from the input unit 42 (Step S16). For example, when an operator of the processing apparatus 4 selects via a mouse a selection field to save the image on a selection menu where the operator can choose to save the processed image, instruction information to save the processed image is input from the input unit 42 to the control unit 41. Further, when the operator of the processing apparatus 4 selects via a mouse a selection field not to save the image, instruction information not to save the processed image is input from the input unit 42 to the control unit 41.

If the control unit 41 determines that the image processed by the image processing unit 45 is not to be saved (Step S16: No), the processing apparatus 4 finishes the image processing. Further, if the control unit 41 determines that the image processed by the image processing unit 45 is to be saved (Step S16: Yes), the processing apparatus 4 saves the processed image in a specified destination to save (Step S18), and finished the image processing in the processing apparatus 4.

Figure 8:
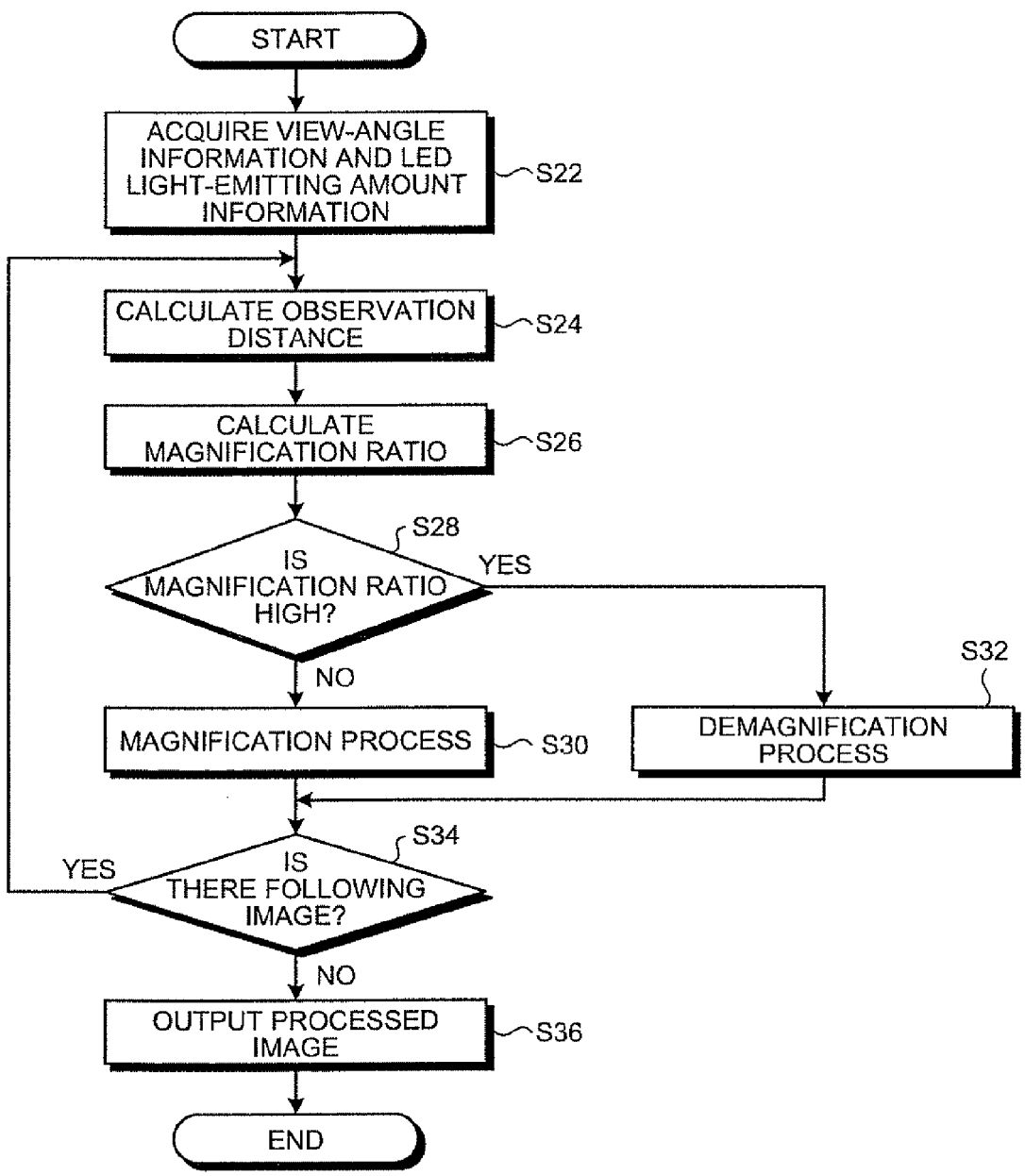
FIG. 8 is a flowchart showing an example of an image processing procedure performed by an image processing unit shown in FIG. 4.

The image processing performed in the image processing unit 45 (Step S12) is described below in a specific manner. Firstly, the image processing where the image processing unit 45 processes the image using the magnification-ratio-adjusting program of the image processing programs shown in FIG. 6 is described as an example with reference to FIG. 8.

The image processing unit 45 acquired view-angle information and LED light-emitting amount information of the imaging unit 22 in the capsule endoscope 2 which has captured the image information to be processed from the type information acquired by the process setting unit 46 according to the procedure of the magnification-ratio-adjusting program (Step S22).

The image processing unit 45 calculates observation distance in the capsule endoscope 2 based on the view-angle information and the LED light-emitting amount information (Step S24). The view angle is a range of the angle for the imaging unit 22 of the capsule endoscope 2 to capture clear images. The observation distance can be calculated based on the view angle. Further, in the capsule endoscope 2, the imaging unit 22 automatically adjusts light. When the imaged area is too dark as an object to be captured is far, the imaging unit 22 automatically increases a light-emitting amount of an LED. When the imaged area is too light as the object to be captured is close, the imaging unit 22 automatically decreases the light-emitting amount of the LED. Thus, the image processing unit 45 can calculate the distance between the object to be captured and the capsule endoscope 2 based on information of the LED light-emitting amount, specifically, the light-emitting amount of the LED at the time when the image information to be processed is captured.

The image processing unit 45 calculates the magnification ratio of the imaging unit 22 in the capsule endoscope 2 which has captured the image to be processed based on the calculated observation distance and the size of the imaged object in the image information to be processed (Step S26).

The image processing unit 45 determines whether the calculated magnification ratio is higher than a predetermined magnification ratio corresponding to an intended usage (Step S28). When the image processing unit 45 processes an image of the inside of the stomach observed by the capsule endoscope 2 for observing the small intestine for the image to be used for the diagnosis, the image processing unit 45 compares the calculated magnification ratio with the magnification ratio of the capsule endoscope 2 for observing the stomach. The compared magnification ratios may be included in the magnification-ratio-adjusting program, or acquired from the optical-information set Dr in the storage unit 44.

If the image processing unit 45 determines that the calculated magnification ratio is not higher than the predetermined magnification ratio (Step S28: No), i.e., that the calculated magnification ratio is lower than the predetermined magnification ratio, the image processing unit 45 magnifies the image to be processed in correspondence with the predetermined magnification ratio (Step S30). For example, when the image to be processed is the image of the inside of the stomach captured by the capsule endoscope 2 for observing the small intestine, and the magnification ratio is lower than the magnification ratio of the capsule endoscope 2 for observing the inside of the stomach, the image processing unit 45 magnifies the capsule endoscope 2 for observing the inside of the stomach.

On the other hand, if the image processing unit 45 determines that the calculated magnification ratio is higher than the predetermined magnification ratio (Step S28: Yes), the image processing unit 45 demagnifies the image to be processed in correspondence with the predetermined magnification ratio (Step S23).

After the magnification process or the demagnification process, the image processing unit 45 determines whether there is a following image to be processed. If the image processing unit 45 determines that there is the following image to be processed (Step S34: Yes), the image processing unit 45 proceeds to Step S24 and calculates observation distance on the image to be processed. On the other hand, if the image processing unit 45 determines that there is not the following image to be processed (Step S34: No), the image processing unit 45 outputs a series of processed images to the control unit 41 (Step S36), and finishes the image processing. The series of images processed by the image processing unit 45 are displayed by the display unit 47, and stored in the database Db and the like via the control unit 41.

Figure 9:
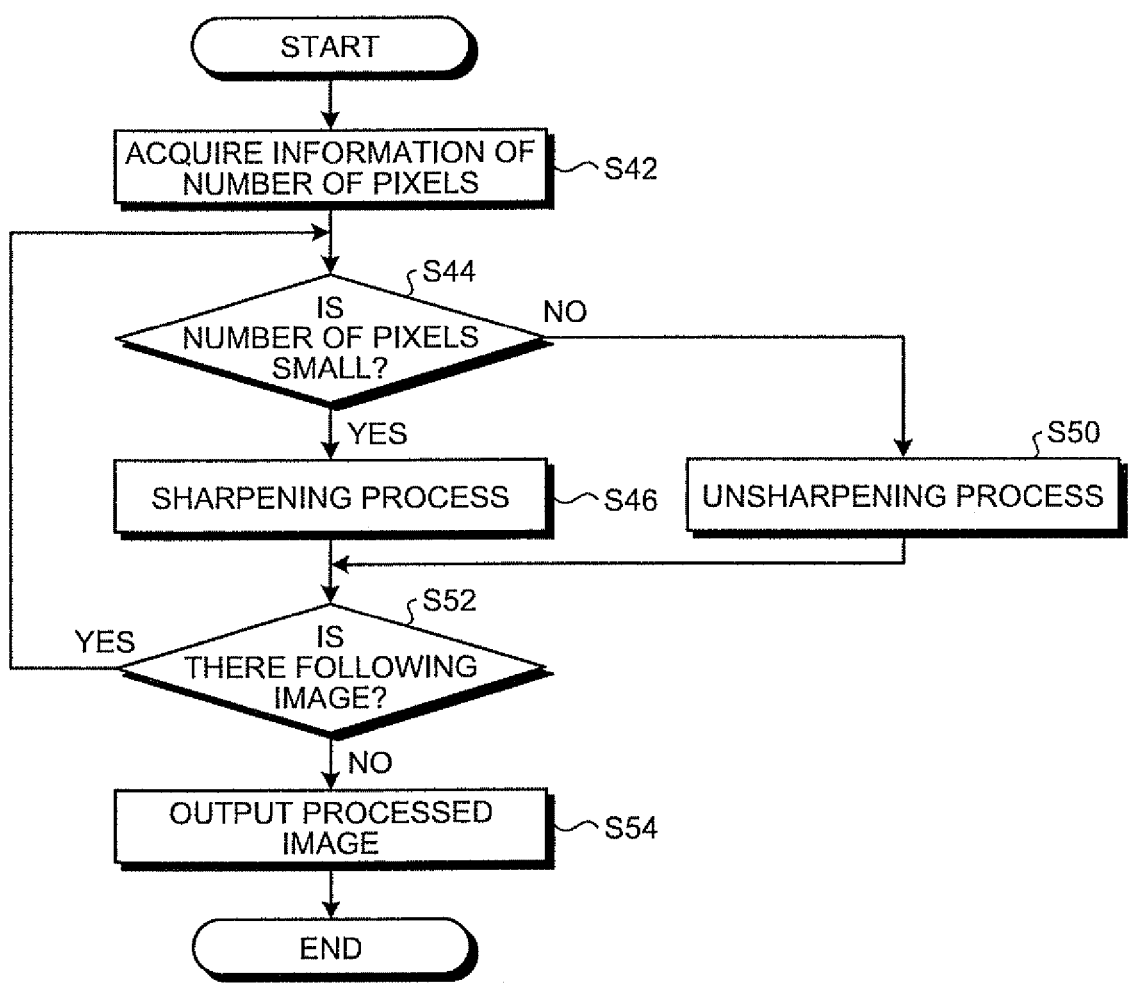
FIG. 9 is a flowchart showing an example of the image processing procedure performed by the image processing unit shown in FIG. 4.

A case where the image processing unit 45 processes images using the sharpening program of the image-processing programs shown in FIG. 6 is described with reference to FIG. 9. According to the procedure of the sharpening program, the image processing unit 45 acquires information of the number of pixels which indicates the number of pixels of the imaging unit 22 of the capsule endoscope 2 which has captured the image to be processed from the type information acquired by the process setting unit 46 (Step S42).

The image processing unit 45 determines, based on the acquired information of the number of pixels, whether the number of pixels of the imaging unit 22 of the capsule endoscope 2 which has captured the image to be processed is smaller than a predetermined number of pixel corresponding to an intended usage (Step S44). For example, when the image processing unit 45 processes the image of the inside of the stomach observed by the capsule endoscope 2 for observing the small intestine for the image to be used for the diagnosis, the image processing unit 45 compares the number of pixels with the number of pixels of the capsule endoscope 2 for observing the inside of the stomach. The compared number of pixels may be included in the sharpening program, or acquired from the optical-information set Dr stored in the storage unit 44.

When the image processing unit 45 determines that the number of pixels of the imaging unit 22 of the capsule endoscope 2 which has captured the image to be processed is smaller than the predetermined number of pixels (Step 44: Yes), the image processing unit 45 sharpens edges of the image to be processed by adjusting the sharpness of the image (Step S46). When the image to be processed is an image of the inside of the stomach captured by the capsule endoscope 2 for observing the small intestine, and the image is captured with the number of pixels which is smaller than the number of pixels of the capsule endoscope for observing the inside of the stomach, the image processing unit 45 sharpens the image in correspondence with the sharpness of the capsule endoscope 2 because the edge of the image is unclear compared with the image captured by the capsule endoscope 2 for observing the inside of the stomach.

On the other hand, when the image processing unit 45 determines that the number of pixels of the imaging unit 22 of the capsule endoscope 2 which has captured the image to be processed is larger than the predetermined number of pixels (Step S44: No), the image processing unit 45 does not sharpen the edge because the sharpness of the image to be processed is clear enough for the intended usage in the diagnosis. Thus, the image processing unit 45 determines the case as "unsharp" (Step S50). When the image to be processed is the image of the inside of the stomach captured by the capsule endoscope 2 for observing the small intestine, and the image is captured with the larger number of pixels than the number of pixels of the capsule endoscope 2 for observing the inside of the stomach, it is not necessary for the image processing unit 45 to sharpen the image in correspondence with the sharpness of the capsule endoscope 2 for observing the inside of the stomach because the edge of the image to be processed is no less clear than the image captured by the capsule endoscope 2 for observing the inside of the stomach.

After the determination process of the sharpening or unsharpening, the image processing unit 45 determines whether there is a following image to be processed (Step S52). If the image processing unit 45 determines that there is the following image to be processed (Step S52: Yes), the image processing unit 45 proceeds to Step S44, and performs a determination process on the number of pixels of the following image to be processed. On the other hand, if the image processing unit 45 determines that there is not the following image to be processed (Step S52: No), the image processing unit 45 outputs the series of processed images to the control unit 41 (Step S54), and finishes the image processing. The series of images processed by the image processing unit 45 are displayed by the display unit 47, and stored in the database Db and the like via the control unit 41.

A care where the image processing unit 45 processes images using the luminance-adjusting program of the image-processing programs shown in FIG. 6 is described as an example with reference to FIG. 10. According to the procedure of the luminance-adjusting program, the image processing unit 45 acquires information related to luminance such as the F-number, the LED light-emitting amount, the LED light-emitting efficiency, and luminance around the lens in the imaging unit 22 of the capsule endoscope 2 which has captured the image information to be processed from the type information acquired by the process setting unit 46 (Step S62).

The image processing unit 45 calculates luminance of a central of the image to be processed based on the F-number, the LED light-emitting amount, the LED light-emitting efficiency, and the luminance around the lens (Step S64). Then, the image processing unit 45 calculates luminance of a predetermined periphery of the center of the image to be processed (Step S66).

The image processing unit 45 compares the calculated luminance of central with the calculated luminance of periphery to determine whether the luminance of center is higher than the luminance of periphery (Step S68). When the image processing unit 45 determines that the luminance of center is higher than the luminance of center (Step S68: Yes), the image processing unit 45 increases a gain of the entire image because the periphery of the image is darker than the center of the image (Step S70) so that the entire image becomes lighter and can be clearly observed. On the other hand, if the image processing unit 45 determines that the luminance of center is lower than the luminance of periphery (Step S68: No), the image processing unit 45 decreases the gain of the entire image because the periphery of the image is lighter than the center of the image (Step S72) so that the entire image becomes darker and can be clearly observed.

After the process of increasing the gain or decreasing the gain, the image processing unit 45 determines whether there is the following image to be processed (Step S74). If the image processing unit 45 determines that there is the following image to be processed (Step S74: Yes), the image processing unit 45 proceeds to Step S62, and acquires information related to luminance of the image to be processed to adjust the luminance. On the other hand, if the image processing unit 45 determines that there is not the following image to be processed (Step S74: No), the image processing unit 45 outputs the series of processed images to the control unit 41 (Step S76), and finishes the image processing. The series of images processed by the image processing unit 45 are displayed by the display unit 47, and stored in the database Db and the like via the control unit 41.

Thus, in the embodiment, the capsule endoscope 2 attaches the type information corresponding to the optical information of the imaging unit 22 in the capsule endoscope 2 to each image, and transmits the images. The processing apparatus 4 processes the image to be processed using the image-processing program corresponding to the optical information of the imaging unit 22 which has captured the image based on the type information attached to the image to be processed. As a result, the processing apparatus 4 can process the images which correspond to portions other than the applied area of the capsule endoscope 2, whereby the images which could not be used as they were can be used for the diagnosis. Thus, according to the present embodiment, the images corresponding to portions other than the applied area which have been wasted conventionally are not wasted and can be used, and a smaller number of images are wasted. Further, conventionally, the subject has to swallow the capsule endoscope corresponding to the organ to be captured so that the images corresponding to portions other than the applied area could be acquired. However, in the present invention, the subject does not have to swallow the capsule endoscope again, whereby the subject takes less burden.

Further, in the present embodiment, the images corresponding to portions other than the applied area of the capsule endoscope 2 in the images stored in the database Db are processed so that the images can be used. Thus, the images in the database Db can be efficiently used. For example, the processing apparatus 4 processes the image of the small intestine captured by the capsule endoscope 2 for previously observing the inside of the stomach of the subject so that the images of the small intestine of the subject currently observed can be compared with the processed image. Thus, the previous observation images can be used as history information of the subject.

Further, in the present embodiment, of the images captured by the capsule endoscope 2 for observing the small intestine, the image at the boundary between the small intestine and the large intestine is processed in correspondence with the optical information of the capsule endoscope 2 for observing the large intestine, whereby even the image captured toward the large intestine, where the inner diameter is smaller than that of the small intestine and the object to be observed is far than that of a case in the small intestine, can be used for the diagnosis more efficiently.

Further, in the present embodiment, the case where the image of the inside of the stomach observed by the capsule endoscope for observing the small intestine is processed as an example. The present invention, however, is not limited to the embodiment. The processing apparatus 4 can process the image selecting the image-processing program which processes the image corresponding to portions other than the applied area of the capsule endoscope 2 to be used. For example, the image of the inside of the large intestine observed by the capsule endoscope 2 for observing the small intestine may be processed in correspondence with the optical information of the capsule endoscope 2 for observing the large intestine. As a result, according to the present embodiment, most of the images of the enteric cavities which are captured by the capsule endoscope 2 can be used for diagnosis.

In the present embodiment, as shown in the table T1, when each version of each type of the capsule endoscope 2 differs corresponding to the optical information, version information may also be used with the type information. In this case, the capsule endoscope 2 attaches the type information of the imaging unit 22 and the version information of the capsule endoscope 2 to each piece of image information, and transmits the image information. In the processing apparatus 4, the process setting unit 46 acquires the type information and also version information attached to the image information to be processed, and acquires the optical information corresponding to the acquired type information and the acquired version information with reference to the table T1, for example. Then, the process setting unit 46 selects the image-processing program corresponding to the acquired optical information from the image-processing-program set Dp, and sets the image-processing program as the image program to process the image information to be processed. Thus, in the present embodiment, when the optical information differs depending on each piece of version information, the type information and the version information may be used for the image processing.

Further, when the different version information is attached depending on each different optical performance of the imaging unit 22, i.e., when the different version information is attached to the different optical information of the imaging unit 22 regardless of the type of the capsule endoscope 2, the optical information can determined by the version information, and the capsule endoscope 2 does not need to further attach the type information. Thus, the capsule endoscope 2 attaches only the version information to the image information, and transmits the image information. In the processing apparatus 4, the storage unit 44 stores the combinations of the optical information corresponding to the version information of the capsule endoscope 2 as the optical-information set Dr, respectively. Then, the process setting unit 46 acquires the version information attached to the image information to be processed, and acquires the optical information corresponding to the acquired version information from the optical-information set Dr. The process setting unit 46 selects the image-processing program corresponding to the acquired optical information from the image-processing-program set Dp, and sets the image-processing program as the image program to process the image information to be processed. Thus, in the present embodiment, when the optical information can be determined only by the version information, the image processing of the image to be processed may be determined only by the version information.

Further, in the present embodiment, the case where the processing apparatus processes the image stored in the database Db or the images acquired via the portable storage medium 5. The present invention, however, is not limited to the case above. For example, the receiving apparatus 3 shown in FIG. 1 may process approximately in real time the images which are successively transmitted from the capsule endoscope 2 approximately real time, and the processed images may be stored in the storage unit in the receiving apparatus 3 or the portable storage medium 5.

In this case, as shown in FIG. 11, the receiving apparatus 3 stores the optical-information set Dr and the image-processing-program set Dp, in the main receiving unit 3b which performs the process on the wireless-transmission signal received via the receiving antennas A1 to An in the wireless-transmission unit 3a. The receiving apparatus 3 processes the image to be processed corresponding to portions other than the applied area of the capsule endoscope 2 using the optical-information-set Dr and the image-processing-program set Dp so that the image can be used.

The main receiving unit 3b is described in detail. As shown in FIG. 11, the main receiving unit 3b includes a receiving unit 31, a converting unit 32, a synchronizing-signal detection unit 33, an image processing unit 34, and a storage unit 36. The receiving unit 31 switches an antenna A for receiving the wireless-transmission signal. The receiving unit 31 performs the receiving process to perform demodulation, analog/digital conversion, and the like on the wireless-transmission signal received via the switched antenna A, and outputs a signal Sa. The converting unit 32 converts the signal Sa which is output from the receiving unit 31 into a signal Si having a signal format which can be processed by the image processing unit 34. The converting unit 32 outputs the signal Si at the same timing of a synchronizing signal output of the synchronizing-signal detection unit 33. The synchronizing-signal detection unit 33 detects each synchronizing signal from the signal Sa, and outputs synchronizing-signal information Sd corresponding to the detected synchronizing signal to the image processing unit.

The image processing unit 34 performs a predetermined process on the signal Si which is output from the converting unit 32, and outputs image data Sf corresponding to a single frame of the image. The storage unit 36 stores the optical-information-set Dr and the image-processing-program set Dp along with the information needed for the image processing in the receiving apparatus 3.

As shown in FIG. 11, the image processing unit 34 includes the process setting unit 46. The process setting unit 46 acquires the optical information corresponding to the type information attached to the image information to be processed from the optical information stored in the storage unit 36. The process setting unit 46 sets the image-processing program, of the image-processing programs stored in the storage unit 44, which corresponds to the acquired optical information as the image-processing program to process the image information to be processed. The image processing unit 34 processes the image to be processed in approximately real time using the image-processing program corresponding to the optical information of the image information to be processed that is set by the process setting unit. Thus, the image which corresponds to portions other than the applied area of the capsule endoscope 2, and which could not be used as they were can be used.

According to the present invention, the body-insertable apparatus attaches the type information corresponding to the optical information of the imaging unit of the body-insertable apparatus to the in-vivo image information, and transmits the image information. The processing apparatus acquires the optical information corresponding to the type information attached to the image information to be processed, and processes the image information to be processed using the image-processing program corresponding to the acquired optical information. The processing apparatus can also process the image information to be processed that corresponds to portions other than the applied area of the body-insertable apparatus so that the image information to be processed can be used. The image which corresponds to portions other than the applied area and which is captured by the body-insertable apparatus can be used for the diagnosis. Further, the subject does not have to swallow the capsule endoscope again.

Additional advantages and modifications will readily occur to those skilled in the art. Therefore, the invention in its broader aspects is not limited to the specific details and representative embodiments shown and described herein.

Accordingly, various modifications may be made without departing from the spirit or scope of the general inventive concept as defined by the appended claims and their equivalents.

INDUSTRIAL APPLICABILITY

As described above, the in-vivo image acquiring system, the in-vivo image processing method, and the body-insertable apparatus according to the present invention are useful for acquiring images of organs which are captured inside the subject, and particularly suitable for decreasing the number of wasted images of organs since the images of organs corresponding to portions other than the applied area can be used for diagnosis as well as the images of organs of the applied area inside the subject that can be properly captured by the imaging unit.

What is claimed is:

1. An in-vivo image acquiring system comprising:
a body-insertable apparatus which is introduced into a subject, and wirelessly transmits image information including captured images of an inside of the subject to an outside of the subject; and
a processing apparatus which processes the image information wirelessly transmitted from the body-insertable apparatus, wherein
the body-insertable apparatus comprises
an imaging unit which captures images of the inside of the subject, and
a transmitting unit which attaches type information which corresponds to optical information in the imaging unit to the image information including the images captured by the imaging unit, and transmits the image information, and
the processing apparatus comprises
a storage unit which stores therein combinations of each piece of the optical information corresponding to each piece of the type information, and image processing programs corresponding to each piece of the optical information, and
an image processing unit which acquires the optical information corresponding to the type information which is attached to the image information to be processed from the optical information stored in the storage unit, and processes the image information to be processed using the image processing program, of the image processing programs stored in the storage unit, which corresponds to the acquired optical information,
wherein
the type information indicates an applied portion of the body-insertable apparatus, and
the image processing unit acquires the optical information corresponding to a portion other than the applied portion of the body-insertable apparatus, and processes the image information corresponding to the portion other than the applied portion of the body-insertable apparatus as the image information to be processed using the image processing program corresponding to the acquired optical information.

2. The in-vivo image acquiring system according to claim 1, wherein
the optical information indicates a magnification ratio of the imaging, a number of pixels, or a luminance in the imaging unit,
the image processing program is a magnification-ratio-adjusting program which changes the magnification ratio of the image to be processed, a sharpening program which changes sharpness of the image to be processed, or a luminance-adjusting program which changes luminance of the image to be processed, and
the image processing unit processes the image information to be processed using the magnification-ratio-adjusting program, the sharpening program, or the luminance-adjusting program based on the magnification ratio of the imaging, the number of pixels, or the luminance corresponding to the type information of the image information to be processed.

3. An in-vivo image processing method for processing image information including images of an inside of a subject which are wirelessly transmitted from a body-insertable apparatus introduced inside the subject, the in-vivo image processing method comprising the steps of:
capturing the images of the inside of the subject by the imaging unit in the body-insertable apparatus;
transmitting the image information to which the type information corresponding to the optical information in the imaging unit is attached from the body-insertable apparatus;
receiving the image information transmitted from the body-insertable apparatus; and
acquiring the optical information corresponding to the type information attached to the image information to be processed from the received image information, and processing the image information to be processed using the image processing program corresponding to the acquired optical information,
wherein
the type information indicates an applied portion of the body-insertable apparatus,
the acquiring step includes acquiring the optical information corresponding to a portion other than the applied portion of the body-insertable apparatus, and
the processing step includes processing the image information corresponding to the portion other than the applied portion of the body-insertable apparatus as the image information to be processed using the information processing program corresponding to the acquired optical information.

4. The in-vivo image processing method according to claim 3, wherein
the optical information indicates a magnification ratio of the imaging, a number of pixels, or a luminance in the imaging unit,
the image processing program is a magnification-ratio-adjusting program which changes the magnification ratio of the image to be processed, a sharpening program which changes sharpness of the image to be processed, or a luminance-adjusting program which changes luminance of the image to be processed, and
the processing step includes processing the image information to be processed using the magnification-ratio-adjusting program, the sharpening program, or the luminance-adjusting program based on the magnification ratio of the capturing, the number of pixels, or the luminance corresponding to the type information of the image information to be processed.

* * * * *